United States Patent
Skeete et al.

(10) Patent No.: US 12,063,315 B2
(45) Date of Patent: Aug. 13, 2024

(54) BLOCKCHAIN-BASED CONSUMABLES MANAGEMENT WITH SUPPORT FOR OFFLINE INSTRUMENTS

(71) Applicant: LEICA BIOSYSTEMS MELBOURNE PTY LTD, Mt. Waverley (AU)

(72) Inventors: Orlando Skeete, Prahran (AU); Zbigniew Mioduszewski, Ringwood North (AU)

(73) Assignee: LEICA BIOSYSTEMS MELBOURNE PTY LTD, Mount Waverley (AU)

( * ) Notice: Subject to any disclaimer, the term of this patent is extended or adjusted under 35 U.S.C. 154(b) by 545 days.

(21) Appl. No.: 17/281,519

(22) PCT Filed: Nov. 26, 2019

(86) PCT No.: PCT/IB2019/060145
§ 371 (c)(1),
(2) Date: Mar. 30, 2021

(87) PCT Pub. No.: WO2020/109980
PCT Pub. Date: Jun. 4, 2020

(65) Prior Publication Data
US 2022/0045869 A1 Feb. 10, 2022

Related U.S. Application Data

(60) Provisional application No. 62/772,932, filed on Nov. 29, 2018.

(51) Int. Cl.
*H04L 9/32* (2006.01)
*G06K 7/14* (2006.01)
(Continued)

(52) U.S. Cl.
CPC .......... *H04L 9/3265* (2013.01); *G06K 7/1417* (2013.01); *G06K 19/06009* (2013.01);
(Continued)

(58) Field of Classification Search
CPC ....... H04L 9/3265; H04L 9/3247; H04L 9/50; G06Q 10/08; G06Q 10/087; G06K 7/1417; G06K 19/06009; G16H 40/20
See application file for complete search history.

(56) References Cited

U.S. PATENT DOCUMENTS

| | | | |
|---|---|---|---|
| 7,349,856 B2* | 3/2008 | Ackermann | G16H 40/20 |
| | | | 705/2 |
| 9,075,906 B2* | 7/2015 | Hyde | G16H 40/67 |

(Continued)

FOREIGN PATENT DOCUMENTS

| | | |
|---|---|---|
| CA | 2 762 821 A1 | 6/2012 |
| CN | 108764797 A | 11/2018 |

(Continued)

OTHER PUBLICATIONS

How blockchains can improve measuring instruments regulation and control, Melo et al, May 2018 (Year: 2018).*

(Continued)

*Primary Examiner* — Jahangir Kabir
(74) *Attorney, Agent, or Firm* — Sughrue Mion, PLLC

(57) ABSTRACT

Blockchain-based consumables management with support for offline instruments. In an embodiment, a user device scans a first machine-readable code on a consumable, scans a second machine-readable code displayed on a display of an instrument that is not communicatively connected to a blockchain network, decodes a consumable code from the first machine-readable code, decodes an instrument code from the second machine-readable code, broadcasts a transaction message, comprising the consumable code and the (Continued)

instrument code, to the blockchain network, receives a use code from the blockchain network, encodes the use code into a third machine-readable code, and displays the third machine-readable code, on a display of the user device, for scanning by the instrument.

19 Claims, 4 Drawing Sheets

(51) Int. Cl.
  *G06K 19/06* (2006.01)
  *G06Q 10/087* (2023.01)
  *G16H 40/20* (2018.01)
  *H04L 9/00* (2022.01)

(52) U.S. Cl.
  CPC .......... *G06Q 10/087* (2013.01); *G16H 40/20* (2018.01); *H04L 9/3247* (2013.01); *H04L 9/50* (2022.05); *H04L 2209/56* (2013.01)

(56) References Cited

U.S. PATENT DOCUMENTS

| | | | |
|---|---|---|---|
| 11,263,641 B2* | 3/2022 | Chantz | G06F 21/64 |
| 2006/0279588 A1 | 12/2006 | Yearworth et al. | |
| 2007/0198213 A1* | 8/2007 | Parvin | G16H 10/40 |
| | | | 702/179 |
| 2011/0188068 A1 | 8/2011 | Jones et al. | |
| 2015/0332283 A1 | 11/2015 | Witchey | |
| 2017/0150329 A1 | 5/2017 | Disilvestro et al. | |
| 2018/0096347 A1 | 4/2018 | Goeringer et al. | |
| 2018/0174292 A1 | 6/2018 | Takamori | |
| 2018/0211059 A1* | 7/2018 | Aunger | G06F 21/6263 |
| 2019/0125361 A1* | 5/2019 | Shelton, IV | A61B 17/1227 |
| 2019/0348158 A1* | 11/2019 | Livesay | H04L 9/3239 |

FOREIGN PATENT DOCUMENTS

| | | |
|---|---|---|
| CN | 112789639 A | 5/2021 |
| JP | 2009-121818 A | 6/2009 |
| JP | 2012-211804 A | 11/2012 |
| JP | 2018-128774 A | 8/2018 |
| KR | 10-1871468 B1 | 6/2018 |
| KR | 10-2021-0041096 A | 4/2021 |
| WO | WO 2020/109980 A1 | 6/2020 |

OTHER PUBLICATIONS

International Preliminary Report on Patentability mailed May 25, 2021 for related International App No. PCT/IB2019/060145, in 6 pages.
International Search Report and Written Opinion dated Mar. 3, 2020 for related International Application No. PCT/IB2019/060145, in 10 pages.
Extended European Search Report issued Apr. 11, 2022 in Application No. 19888503.0.
Office Action issued Jan. 10, 2023 in Indian Application No. 202147024687.
Office Action issued Jul. 30, 2023 in Korean Application No. 10-2021-7009462.
Chinese Office Action dated Dec. 11, 2023 in Application No. 201980064381.0.

* cited by examiner

BLOCKCHAIN-BASED CONSUMABLES MANAGEMENT WITH SUPPORT FOR OFFLINE INSTRUMENTS

CROSS-REFERENCE TO RELATED APPLICATIONS

This application is the national stage of International Patent App. No. PCT/IB2019/060145, filed on Nov. 26, 2019, which claims priority to U.S. Provisional Patent App. No. 62/772,932, filed on Nov. 29, 2018, which are both incorporated herein by reference as if set forth in full.

BACKGROUND

Field of the Invention

The embodiments described herein are generally directed to consumables management, and, more particularly, to blockchain-based consumables management which supports usage of consumables in offline instruments.

Description of the Related Art

Blockchain technology is a promising tool in the context of asset management. Specifically, the use of a modification-resistant ledger (i.e., implemented as the blockchain) practically ensures accurate and immutable tracking of assets.

Such tracking would be especially useful in the tracking of consumables, such as the reagents offered by Leica Biosystems™. Typically, a manufacturer will sell or lease expensive instruments (e.g., tissue processing systems, stainers, etc.) to customers (e.g., medical professionals) for low or no cost, and recoup the cost of the instruments by selling the customers consumables, such as individual reagents, reagent kits (e.g., which utilize a set of individual reagents in fixed counts and/or ratios), bulk reagents, and/or the like, for use in the instruments. Thus, it would be beneficial if such manufacturers could ensure that only their consumables are being used with their instruments.

In addition, certain consumables may be regulated by the government. For example, in the U.S., certain consumables are regulated by the Food and Drug Administration (FDA). For example, reagents utilized for diagnosing cancer are classified as Class III reagents, and are heavily regulated by the FDA. The reason for such heavy regulation is that human lives literally depend on the quality of reagents being used for diagnosis. Thus, for safety reasons, it would also be beneficial if manufacturers could better manage recalls of defective consumables and prevent the use of counterfeit consumables.

However, the medical context presents unique privacy concerns for asset tracking. Specifically, many of the instruments that utilize such consumables process individually identifiable health information, governed, for example, by the Health Insurance Portability and Accountability Act (HIPAA). For this reason, such instruments are frequently maintained offline to protect such information from network-based cyberattacks or other misuse. In this case, "offline" does not necessarily mean that the instrument is not connected to any network, but rather that the instrument is not connected (either temporarily or permanently) to the blockchain network which processes the transactions necessary for blockchain-based asset management.

SUMMARY

Accordingly, systems, methods, and non-transitory computer-readable media are disclosed for blockchain-based consumables management with support for offline instruments.

In an embodiment, a method is disclosed that comprises using at least one hardware processor of a user device to: scan a first machine-readable code on a consumable; scan a second machine-readable code displayed on a display of an instrument that is not communicatively connected to a blockchain network; decode a consumable code from the first machine-readable code; decode an instrument code from the second machine-readable code; broadcast a transaction message, comprising the consumable code and the instrument code, to the blockchain network; receive a use code from the blockchain network; encode the use code into a third machine-readable code; and display the third machine-readable code, on a display of the user device, for scanning by the instrument.

In an embodiment, the method further comprises using at least one hardware processor of the instrument to: scan the third machine-readable code displayed on the display of the user device; decode the use code from the third machine-readable code; validate the use code; utilize the consumable for one or more runs; store usage information for the one or more runs in a memory of the instrument; and, at a subsequent time, generate a fourth machine-readable code that encodes the instrument code and the stored usage information, and display the fourth machine-readable code on the display of the instrument for scanning by a user device. This method may further comprise using at least one hardware processor of a user device to: scan the fourth machine-readable code displayed on the display of the instrument; decode the usage information from the fourth machine-readable code; and broadcast one or more transaction messages, comprising the consumable code and the usage information to the blockchain network. This method may further comprise providing software to be executed on each of a plurality of nodes of the blockchain network, wherein the software, when executed by at least one hardware processor of a node: receives the one or more transaction messages from the user device; and adds a usage transaction to a block in a blockchain managed by the blockchain network, wherein the usage transaction associates the consumable code with the usage information. The use code may indicate one or more restrictions, wherein the method further comprises using the at least one hardware processor of the instrument to limit the utilization of the consumable according to the one or more restrictions. The one or more restrictions may comprise a number of runs, wherein limiting the utilization of the consumable comprises limiting the one or more runs so as not to exceed the number of runs in the one or more restrictions. The one or more restrictions may comprise a recall for one or more types of runs, wherein limiting the utilization of the consumable comprises prohibiting the one or more types of runs. The one or more types of runs may comprise a type of test.

In an embodiment, the method further comprises providing software to be executed on each of a plurality of nodes of the blockchain network, wherein the software, when executed by at least one hardware processor of a node: receives the transaction message from the user device; validates the transaction message; and when the transaction message is validated, adds a transaction to a block in a blockchain managed by the blockchain network, generates the use code based on the transaction, and sends the use code to the user device. The transaction may associate the consumable code with the instrument code. Validating the transaction message may comprise verifying whether or not the consumable code is valid. Verifying that the consumable code is valid may comprise: searching the blockchain for an origination transaction that indicates the consumable code was created by a valid manufacturer; and, when the origination transaction is identified, verifying that the consumable code is valid. Validating the transaction message may comprise verifying that the consumable code is associated with a predetermined amount of cryptocurrency. Validating the transaction message may comprise verifying that an electronic wallet, associated with an operator of the user device, comprises a predetermined amount of cryptocurrency.

In an embodiment, the consumable comprises a reagent. The consumable may comprise a reagent kit. The instrument may comprise a tissue processing system.

In an embodiment, the method further comprises using at least one hardware processor of the instrument to: detect whether the instrument is communicatively connected to the blockchain network; when the instrument is detected to be communicatively connected to the blockchain network, perform online processing comprising scanning a machine-readable code on a consumable, decoding a consumable code from that machine-readable code, broadcasting a transaction message, comprising the consumable code and the instrument code, to the blockchain network, receiving a use code, validating the use code, utilizing the consumable for one or more runs, and broadcasting a transaction message, comprising usage information for the one or more runs, to the blockchain network; and, when the instrument is detected to not be communicatively connected to the blockchain network, perform offline processing comprising scanning a machine-readable code displayed on a display of a user device, decoding a use code from that machine-readable code, validating the use code, utilizing the consumable for one or more runs, and storing usage information for the one or more runs in a memory of the instrument for future recordation by the blockchain network.

In an embodiment, the method further comprises providing software to be executed on each of a plurality of nodes of the blockchain network, wherein the software, when executed by at least one hardware processor of a node: receives a plurality of transaction messages, wherein each of the plurality of transaction messages represents a scan of the first machine-readable code at a waypoint within a supply chain; and, for each of the plurality of transaction messages, adds a transaction to a block in a blockchain managed by the blockchain network, wherein each transaction associates the consumable code with a time and location. Each transaction may further associate the consumable code with a temperature.

Any of these methods may be embodied in executable software modules of a processor-based system, such as a server, and/or in executable instructions stored in a non-transitory computer-readable medium.

BRIEF DESCRIPTION OF THE DRAWINGS

The details of the present invention, both as to its structure and operation, may be gleaned in part by study of the accompanying drawings, in which like reference numerals refer to like parts, and in which.

DETAILED DESCRIPTION

In an embodiment, systems, methods, and non-transitory computer-readable media are disclosed for blockchain-based consumables management with support for offline instruments. While the disclosed embodiments will primarily be described herein with reference to reagents (e.g., reagent kits or containers), the disclosed embodiments may be used with any type of consumable.

After reading this description, it will become apparent to one skilled in the art how to implement the invention in various alternative embodiments and alternative applications. However, although various embodiments of the present invention will be described herein, it is understood that these embodiments are presented by way of example and illustration only, and not limitation. As such, this detailed description of various embodiments should not be construed to limit the scope or breadth of the present invention as set forth in the appended claims.

1. System Overview 1.1. Infrastructure

Figure 1:
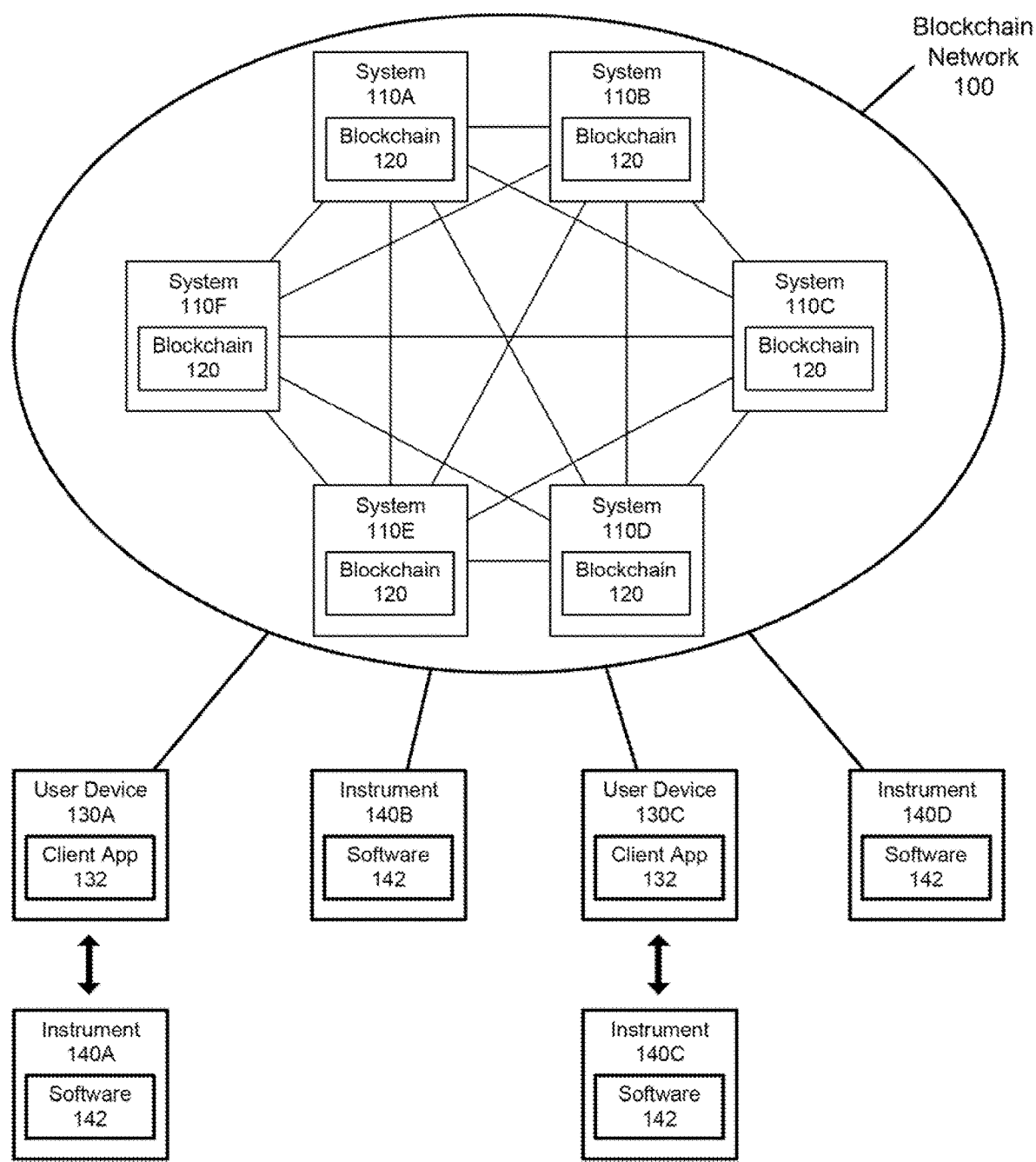
FIG. 1 is a block diagram that illustrates an example infrastructure, in which one or more of the processes described herein, may be implemented, according to an embodiment.

FIG. 1 illustrates an example system for blockchain-based consumables management with support for offline instruments, according to an embodiment. The backbone of the consumables management is blockchain network 100. Blockchain network 100 may comprise a plurality of systems 110 connected as nodes in a peer-to-peer network. Systems 110 may be connected via any wired or wireless, public or private, network or networks, including the Internet, and may communicate via any standard or proprietary communication protocols. Systems 110 may comprise the networked computers (e.g., personal computers, servers, etc.) of the manufacturer(s) of the consumables, their customers (i.e., purchasers of the consumables), and/or third parties. In an embodiment, blockchain network 100 may be implemented using open-source technology, such as Hyperledger Fabric™ by IBM™.

Each node (i.e., system 110) within blockchain network 100 comprises a complete copy of blockchain 120. Blockchain 120 represents a public ledger of all transactions involving the consumables being managed by blockchain network 100. These transactions may comprise purchases of consumables, shipment waypoints for shipped consumables (e.g., origination, intermediate, destination scans, etc.), each partial or complete consumption of consumables, recalls of consumables, registration and deregistration of consumables to parties and/or instruments, and/or the like. Each transaction may identify one or more parties, a location (e.g., location of the scan or other event which produced the transaction), and a time (e.g., a timestamp representing the day and time of the scan or other event which produced the transaction).

As is well-known in the art, blockchain 120 is an open, distributed ledger that is resistant to modification. Specifically, blockchain 120 comprises a plurality of chronologically arranged blocks that are chained together using cryptography. As transactions are created, batches of valid transactions are packaged into a new block along with a cryptographic hash of the most recent block added to blockchain 120. A cryptographic hash of the new block is then generated and the new block with its cryptographic hash is added to blockchain 120. In theory, blockchain 120 could be altered. However, since the blocks are chained together via their cryptographic hashes, in order to alter blockchain 120, the entire blockchain 120 would need to be recomputed, thereby rendering such an undertaking computationally impractical.

Within blockchain network 100, each node (i.e., system 110) is capable of validating transactions, generating new blocks, and broadcasting generated blocks to the other nodes. Since multiple nodes may generate and broadcast new blocks, a consensus method is used to select the next block to be added to blockchain 120. For example, in a blockchain that uses a proof-of-work method, temporary forks may result with different nodes having different versions of blockchain 120, but eventually the chain with the most cumulative proof-of-work will win out. In an embodiment, blockchain network 100 utilizes a proof-of-stake method, in which a node is selected to produce the next valid block in blockchain 120, based on the node's stake (e.g., wealth and/or age) in blockchain 120. Proof-of-stake methods prevent malicious actors by ensuring that they have a stake in the integrity of blockchain 120.

Generally, blockchain 120 is open and viewable by anyone with access to a system 110 storing a copy of blockchain 120. However, the parties to each transaction may be anonymous. In an embodiment, software may be provided (e.g., in a client application 132) that allows a particular user to view, search, and otherwise organize or manage all transactions pertaining to that user on blockchain 120 (e.g., all transactions involving that user's electronic "wallet" address or other identifier), in a convenient, permissions-based graphical user interface. Thus, all manufacturing and logistics information for a customer's consumables are visible to the customer, and the customer can check the status of all of the consumables in the customer's inventory (e.g., registered to the customer by a registration transaction recorded in blockchain 120). Blockchain 120 can also be used as evidence of the valid usage of reagents by customers (e.g., to be provided to the U.S. Food & Drug Administration (FDA)) to provide a regulatory validated system.

User device(s) 130 communicate with blockchain network 100 via wired or wireless, public or private, network or networks, including the Internet. User device(s) 130 may comprise any type or types of computing devices capable of wired and/or wireless communication, including without limitation, desktop computers, laptop computers, tablet computers, smart phones or other mobile phones, servers, game consoles, televisions, set-top boxes, electronic kiosks, point-of-sale terminals, and/or the like. However, in a preferred embodiment, user device(s) 130 comprise a wireless device (e.g., smartphone or tablet) that communicates over a wireless network (e.g., cellular and/or Wi-Fi™ network) and comprises a camera or other device (e.g., laser scanner, for example, housed in a wand) capable of reading machine-readable codes. Each user device 130 may store and execute a client application 132, which implements one or more of the functions described herein.

Instrument(s) 140 consume the consumables (e.g., reagents, including bulk reagents) described herein. For example, instrument(s) 140 may comprise the tissue processing systems and/or staining systems provided by Leica Biosystems™. As an example, instrument 140 may comprise the BOND-III Fully Automated IHC and ISH Stainer from Leica Biosystems™, and the consumables may comprise the DS9800 Bond Polymer Refine Detection Kit, DS9390 Bond Polymer Refine Red Detection Kit, DS9477 ChromoPlex 1 Dual Detection for Bond Kit, AR0833 3.75 mL Bond Anti-Fluorescein Ab Bond ready-to-use Reagent, AR9222 Bond Dewax Solution Bond ready-to-use Reagent, AR9432 Bond DAB Enhancer 30 mL Bond ready-to-use Reagent, AR0222 15 mL Bond Anti-Fluorescein Ab Bond ready-to-use Reagent, AR0633 3.75 mL Stringency Wash Solution Bond ready-to-use Reagent, AR9013 100 mL Bond Hybridization Solution Bond ready-to-use Reagent, AR0584 7.5 mL Anti-Biotin Antibody Bond ready-to-use Reagent, AR9551 Bond Enzyme Pretreatment Kit, AR9590 Bond™ Wash Solution 10× Concentrate 1 L Reagent, AR9352 Bond™ Primary Antibody Diluent 0.5 L Reagent, AR9640 Bond™ Epitope Retrieval 2-1 L Reagent, and/or AR9961 Bond™ Epitope Retrieval 1-1 L Reagent. For privacy or other reasons, some instruments, such as instruments 140A and 140C, may be offline, such that they are not able to communicate with blockchain network 100. Other instruments, such as instruments 140B and 140D, may be online, such that they are able to communicate with blockchain network 100 via wired or wireless, public or private, network or networks, including the Internet. In either case, each instrument 140 may store and execute software 142, which implements one or more of the functions described herein, including separate processes depending on whether the instrument 140 is online or offline.

In an embodiment, blockchain 120 utilizes a cryptocurrency, similar to Bitcoin, referred to herein as "kitcoin." Kitcoins may be transferred between the electronic wallets of parties. In an embodiment, kitcoins may also be mined, in order to provide parties an incentive to lend their computational resources to blockchain network 100. In addition, kitcoins may be consumed (e.g., transferred from customers to manufacturers) as consumables are consumed. For example, a particular amount of kitcoin may be associated with each use of a consumable (e.g., each test or other run of a reagent or reagent kit). As a customer uses a consumable, the appropriate amount of kitcoins (i.e., representing the amount of use) may be transferred from the customer's electronic wallet to the manufacturer's electronic wallet. As used herein, an "amount of kitcoin," "number of kitcoins," or any other reference to a kitcoin or kitcoins, whether singular or plural, may refer to multiple kitcoins or a fractional portion of a single kitcoin.

In an embodiment, each consumable code may initially be associated with an amount of kitcoins. The kitcoins associated with a consumable code may correspond to the number of uses (e.g., runs, doses, tests, etc.) for which the associated consumable is rated. For example, if one kitcoin is associated with one-thousand uses, and a particular consumable (e.g., reagent kit) is rated for one-thousand tests, that consumable would be associated with one kitcoin. Similarly, a particular consumable that is rated for three-thousand tests would be associated with three kitcoins, and a particular consumable that is rated for five hundred tests would be associated with one half of a kitcoin. Once all kitcoins associated with a consumable code have been depleted (i.e., the associated amount of kitcoin is zero), blockchain network 100 may prevent any new transactions involving that consumable code. In an embodiment, because no new transactions can be created for the depleted consumable code, the consumable can no longer be registered and used with any instrument 140. This prevents customers or third parties from refilling empty consumable containers with counterfeit consumables and using or reselling those counterfeit consumables.

1.2. Example Processing Device

Figure 2:
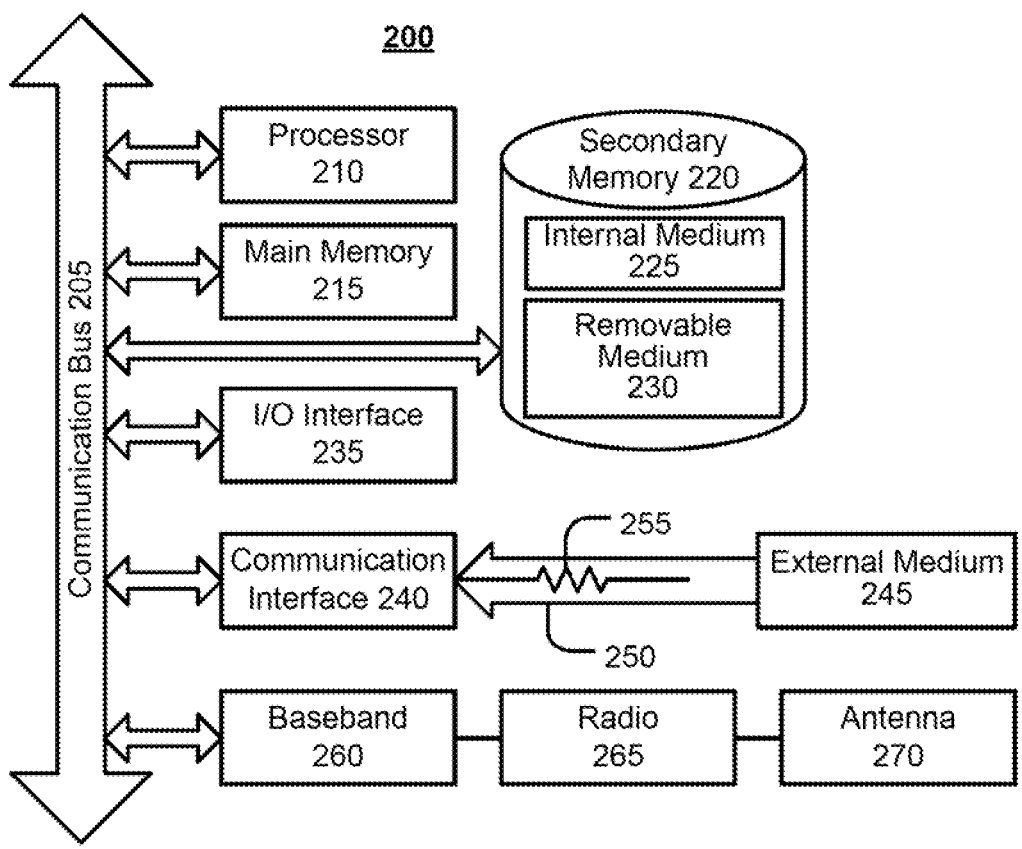
FIG. 2 is a block diagram that illustrates an example processing system, by which one or more of the processed described herein, may be executed, according to an embodiment.

FIG. 2 is a block diagram illustrating an example wired or wireless system 200 that may be used in connection with various embodiments described herein. For example, system 200 may be used as or in conjunction with one or more of the functions, processes, or methods (e.g., to store and/or execute client application 132 and/or software 142, or one or more modules of client application 132 and/or software 142) described herein, and may represent components of platform 110, user device(s) 130, instrument(s) 140, and/or other processing devices described herein. System 200 can be a server or any conventional personal computer, or any other processor-enabled device that is capable of wired or wireless data communication. Other computer systems and/or architectures may be also used, as will be clear to those skilled in the art.

System 200 preferably includes one or more processors, such as processor 210. Additional processors may be provided, such as an auxiliary processor to manage input/output, an auxiliary processor to perform floating-point mathematical operations, a special-purpose microprocessor having an architecture suitable for fast execution of signal-processing algorithms (e.g., digital-signal processor), a slave processor subordinate to the main processing system (e.g., back-end processor), an additional microprocessor or controller for dual or multiple processor systems, and/or a coprocessor. Such auxiliary processors may be discrete processors or may be integrated with processor 210. Examples of processors which may be used with system 200 include, without limitation, the Pentium® processor, Core i7® processor, and Xeon® processor, all of which are available from Intel Corporation of Santa Clara, California.

Processor 210 is preferably connected to a communication bus 205. Communication bus 205 may include a data channel for facilitating information transfer between storage and other peripheral components of system 200. Furthermore, communication bus 205 may provide a set of signals used for communication with processor 210, including a data bus, address bus, and/or control bus (not shown). Communication bus 205 may comprise any standard or non-standard bus architecture such as, for example, bus architectures compliant with industry standard architecture (ISA), extended industry standard architecture (EISA), Micro Channel Architecture (MCA), peripheral component interconnect (PCI) local bus, standards promulgated by the Institute of Electrical and Electronics Engineers (IEEE) including IEEE 488 general-purpose interface bus (GPIB), IEEE 696/S-100, and/or the like.

System 200 preferably includes a main memory 215 and may also include a secondary memory 220. Main memory 215 provides storage of instructions and data for programs executing on processor 210, such as one or more of the functions and/or modules discussed herein. It should be understood that programs stored in the memory and executed by processor 210 may be written and/or compiled according to any suitable language, including without limitation C/C++, Java, JavaScript, Perl, Visual Basic, .NET, and the like. Main memory 215 is typically semiconductor-based memory such as dynamic random access memory (DRAM) and/or static random access memory (SRAM). Other semiconductor-based memory types include, for example, synchronous dynamic random access memory (SDRAM), Rambus dynamic random access memory (RDRAM), ferroelectric random access memory (FRAM), and the like, including read only memory (ROM).

Secondary memory 220 may optionally include an internal medium 225 and/or a removable medium 230. Removable medium 230 is read from and/or written to in any well-known manner. Removable storage medium 230 may be, for example, a magnetic tape drive, a compact disc (CD) drive, a digital versatile disc (DVD) drive, other optical drive, a flash memory drive, and/or the like.

Secondary memory 220 is a non-transitory computer-readable medium having computer-executable code (e.g., disclosed software modules) and/or other data stored thereon. The computer software or data stored on secondary memory 220 is read into main memory 215 for execution by processor 210.

In alternative embodiments, secondary memory 220 may include other similar means for allowing computer programs or other data or instructions to be loaded into system 200. Such means may include, for example, a communication interface 240, which allows software and data to be transferred from external storage medium 245 to system 200. Examples of external storage medium 245 may include an external hard disk drive, an external optical drive, an external magneto-optical drive, and/or the like. Other examples of secondary memory 220 may include semiconductor-based memory, such as programmable read-only memory (PROM), erasable programmable read-only memory (EPROM), electrically erasable read-only memory (EEPROM), and flash memory (block-oriented memory similar to EEPROM).

As mentioned above, system 200 may include a communication interface 240. Communication interface 240 allows software and data to be transferred between system 200 and external devices (e.g. printers), networks, or other information sources. For example, computer software or executable code may be transferred to system 200 from a network server (e.g., platform 110) via communication interface 240. Examples of communication interface 240 include a built-in network adapter, network interface card (NIC), Personal Computer Memory Card International Association (PCM-CIA) network card, card bus network adapter, wireless network adapter, Universal Serial Bus (USB) network adapter, modem, a wireless data card, a communications port, an infrared interface, an IEEE 1394 fire-wire, and any other device capable of interfacing system 200 with a network (e.g., network(s) 120) or another computing device. Communication interface 240 preferably implements industry-promulgated protocol standards, such as Ethernet IEEE 802 standards, Fiber Channel, digital subscriber line (DSL), asynchronous digital subscriber line (ADSL), frame relay, asynchronous transfer mode (ATM), integrated digital services network (ISDN), personal communications services (PCS), transmission control protocol/Internet protocol (TCP/IP), serial line Internet protocol/point to point protocol (SLIP/PPP), and so on, but may also implement customized or non-standard interface protocols as well.

Software and data transferred via communication interface 240 are generally in the form of electrical communication signals 255. These signals 255 may be provided to communication interface 240 via a communication channel 250. In an embodiment, communication channel 250 may be a wired or wireless network (e.g., network(s) 120), or any variety of other communication links. Communication channel 250 carries signals 255 and can be implemented using a variety of wired or wireless communication means including wire or cable, fiber optics, conventional phone line, cellular phone link, wireless data communication link, radio frequency ("RF") link, or infrared link, just to name a few.

Computer-executable code (e.g., computer programs, such as the disclosed application, or software modules) is stored in main memory 215 and/or secondary memory 220. Computer programs can also be received via communication interface 240 and stored in main memory 215 and/or secondary memory 220. Such computer programs, when executed, enable system 200 to perform the various functions of the disclosed embodiments as described elsewhere herein.

In this description, the term "computer-readable medium" is used to refer to any non-transitory computer-readable storage media used to provide computer-executable code and/or other data to or within system 200. Examples of such media include main memory 215, secondary memory 220 (including internal memory 225, removable medium 230, and external storage medium 245), and any peripheral device communicatively coupled with communication interface 240 (including a network information server or other network device). These non-transitory computer-readable media are means for providing executable code, programming instructions, software, and/or other data to system 200.

In an embodiment that is implemented using software, the software may be stored on a computer-readable medium and loaded into system 200 by way of removable medium 230, I/O interface 235, or communication interface 240. In such an embodiment, the software is loaded into system 200 in the form of electrical communication signals 255. The software, when executed by processor 210, preferably causes processor 210 to perform one or more of the processes and functions described elsewhere herein.

In an embodiment, I/O interface 235 provides an interface between one or more components of system 200 and one or more input and/or output devices. Example input devices include, without limitation, sensors, keyboards, touch screens or other touch-sensitive devices, biometric sensing devices, computer mice, trackballs, pen-based pointing devices, and/or the like. Examples of output devices include, without limitation, other processing devices, cathode ray tubes (CRTs), plasma displays, light-emitting diode (LED) displays, liquid crystal displays (LCDs), printers, vacuum fluorescent displays (VFDs), surface-conduction electron-emitter displays (SEDs), field emission displays (FEDs), and/or the like. In some cases, an input and output device may be combined, such as in the case of a touch panel display (e.g., in a smartphone, tablet, or other mobile device).

System 200 may also include optional wireless communication components that facilitate wireless communication over a voice network and/or a data network (e.g., in the case of user system 130). The wireless communication components comprise an antenna system 270, a radio system 265, and a baseband system 260. In system 200, radio frequency (RF) signals are transmitted and received over the air by antenna system 270 under the management of radio system 265.

In an embodiment, antenna system 270 may comprise one or more antennae and one or more multiplexors (not shown) that perform a switching function to provide antenna system 270 with transmit and receive signal paths. In the receive path, received RF signals can be coupled from a multiplexor to a low noise amplifier (not shown) that amplifies the received RF signal and sends the amplified signal to radio system 265.

In an alternative embodiment, radio system 265 may comprise one or more radios that are configured to communicate over various frequencies. In an embodiment, radio system 265 may combine a demodulator (not shown) and modulator (not shown) in one integrated circuit (IC). The demodulator and modulator can also be separate components. In the incoming path, the demodulator strips away the RF carrier signal leaving a baseband receive audio signal, which is sent from radio system 265 to baseband system 260.

If the received signal contains audio information, then baseband system 260 decodes the signal and converts it to an analog signal. Then the signal is amplified and sent to a speaker. Baseband system 260 also receives analog audio signals from a microphone. These analog audio signals are converted to digital signals and encoded by baseband system 260. Baseband system 260 also encodes the digital signals for transmission and generates a baseband transmit audio signal that is routed to the modulator portion of radio system 265. The modulator mixes the baseband transmit audio signal with an RF carrier signal, generating an RF transmit signal that is routed to antenna system 270 and may pass through a power amplifier (not shown). The power amplifier amplifies the RF transmit signal and routes it to antenna system 270, where the signal is switched to the antenna port for transmission.

Baseband system 260 is also communicatively coupled with processor 210, which may be a central processing unit (CPU). Processor 210 has access to data storage areas 215 and 220. Processor 210 is preferably configured to execute instructions (i.e., computer programs, such as the disclosed application, or software modules) that can be stored in main memory 215 or secondary memory 220. Computer programs can also be received from baseband processor 260 and stored in main memory 210 or in secondary memory 220, or executed upon receipt. Such computer programs, when executed, enable system 200 to perform the various functions of the disclosed embodiments.

2. Process Overview

Embodiments of processes for blockchain-based consumables management with support for offline instruments will now be described in detail. It should be understood that the described processes may be embodied in one or more software modules that are executed by one or more hardware processors (e.g., processor 210), for example, as the software applications discussed herein (e.g., client application 132 and/or software 142). The described process may be implemented as instructions represented in source code, object code, and/or machine code. These instructions may be executed directly by the hardware processor(s), or alternatively, may be executed by a virtual machine operating between the object code and the hardware processors. In addition, the disclosed application may be built upon or interfaced with one or more existing systems.

Alternatively, the described processes may be implemented as a hardware component (e.g., general-purpose processor, integrated circuit (IC), application-specific integrated circuit (ASIC), digital signal processor (DSP), field-programmable gate array (FPGA) or other programmable logic device, discrete gate or transistor logic, etc.), combination of hardware components, or combination of hardware and software components. To clearly illustrate the interchangeability of hardware and software, various illustrative components, blocks, modules, circuits, and steps are described herein generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a component, block, module, circuit, or step is for ease of description. Specific functions or steps can be moved from one component, block, module, circuit, or step to another without departing from the invention.

2.1. Consumables Tracking

Figure 3:
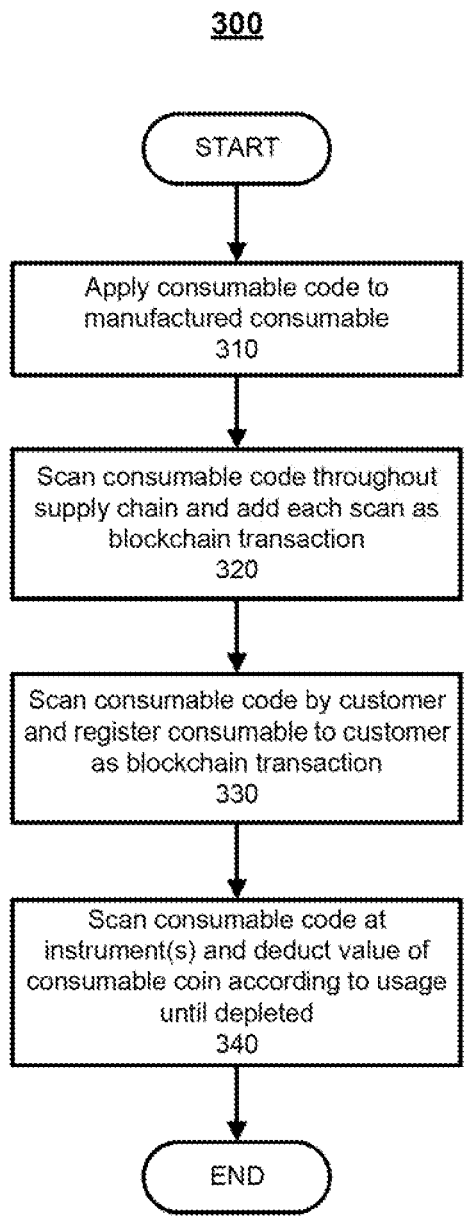
FIG. 3 is a flowchart that illustrates a process for blockchain-based consumables tracking, according to an embodiment.

FIG. 3 is a flowchart that illustrates a process 300 for blockchain-based consumables tracking, according to an embodiment. While process 300 is illustrated with a certain arrangement and ordering of steps, process 300 may be implemented with fewer, more, or different steps and a different arrangement and/or ordering of steps.

In step 310, after a consumable (e.g., reagent or reagent kit) has been manufactured, a unique consumable code is applied to the manufactured consumable. To ensure a closed system that prevents counterfeits and improper usage, two different consumables should never have the same consumable code. Each consumable code may be encoded into a machine-readable code, such as a barcode or Quick Response (QR) code, that is visible on the container of the associated consumable. It should be understood that, because the underlying consumable codes are unique, the machine-readable codes for each consumable will also be unique, such that no consumables are associated with the same machine-readable code.

In the context of a reagent, the machine-readable code, encoding its unique consumable code, may be printed on a label that is applied to a reagent container or printed directly on the reagent container. The machine-readable code for a reagent may encode a lot number, reagent type, volume, and/or the like, and may be readable by an instrument 140 during use (or the container may comprise two machine-readable codes, one of which can be scanned by a user device 140 and one of which can be scanned by instrument 140 during use).

In the context of a reagent kit, comprising a plurality of reagent containers, the machine-readable code, encoding the kit's unique consumable code, may be printed on a label that is applied to the kit carrier or printed directly on the kit carrier. The machine-readable code for the reagent kit may be based on the machine-readable codes for each of the reagent containers within the reagent kit. For example, the machine-readable code for the reagent kit may comprise an encoded combination of the information encoded in each of the machine-readable codes of the reagent containers within the reagent kit.

In step 320, the consumable code that has been applied to the consumable is scanned at each waypoint throughout the supply chain. Waypoints may include the origination point of a shipment (e.g., manufacturer's facility), intermediate transfers within the distribution chain (e.g., arrivals and departures at one or more distribution facilities), and the destination point of the shipment (e.g., customer's facility). Each scan may comprise a manual scan (e.g., using a camera, laser scanning wand, etc., of a user device 130) or an automatic scan (e.g., by a machine at a distribution facility). Each scan may be communicated to blockchain network 100, in real time or near real time, as a transaction to be incorporated into a new block on blockchain 120.

In an embodiment, before a transaction, involving a consumable code, is added to blockchain 120, blockchain network 100 may first confirm that the consumable code is a valid consumable code. A valid consumable code is one that has been issued by an approved manufacturer, has a positive, non-zero number of kitcoins associated with it, and/or the like. Specifically, a node (i.e., system 110) in blockchain network 100 may refer to its copy of blockchain 120 to ensure that the consumable code appears in an origination transaction from the manufacturer, compute the number of kitcoins associated with the consumable code by counting the number of used kitcoins across all usage transactions to ensure that there is still a number of kitcoins associated with the consumable code, and/or the like.

In step 330, the consumable code that has been applied to the consumable is scanned by the customer who receives the consumable (e.g., at the destination point of the shipment). The scan may comprise a manual or an automatic scan, and is communicated to blockchain network 100, in real time or near real time, as a transaction to be incorporated into a new block on blockchain 120. In an embodiment, the transaction may comprise a transfer of the consumable, represented by the consumable code, from the manufacturer to the customer (e.g., from an electronic wallet of the manufacturer to an electronic wallet of the customer). In other words, the consumable is registered with the customer in the blockchain.

In step 340, the consumable code is scanned when used with a particular instrument. The scan may comprise a manual or an automatic scan. For online instruments (e.g., instruments 140B and 140D in FIG. 1), the instrument 140 may scan the consumable code. This scan may be performed manually using a wand or other scanning device attached or integral to instrument 140, or automatically by instrument 140 after the consumable has been loaded into instrument 140. For offline instruments (e.g., instruments 140A and 140C in FIG. 1), the consumable code and an instrument code may be scanned by a user device 130 to obtain a use code, as described in an embodiment with respect to FIG. 4. In either case, each scan is communicated to blockchain network 100 as a transaction to be incorporated into a new block on blockchain 120. The transaction may take the form of a registration transaction that comprises the consumable code and an instrument code uniquely identifying the instrument 140 with which the consumable is to be used.

In an embodiment, blockchain network 100 may prevent any further registration transactions for that consumable code (e.g., registering the consumable code to a different instrument code), until a deregistration transaction is recorded on the blockchain that identifies the consumable code and the registered instrument code. This requirement for a deregistration transaction can be especially useful in the case of offline instruments 140, since it ensures an opportunity to provide offline usage information (i.e., representing usage of consumables between the registration transaction and the deregistration transaction) to blockchain network 100 (i.e., with the deregistration transaction). Specifically, a customer cannot avoid sending the offline usage information to blockchain network 100 to be added as transaction(s) to blockchain 120, since doing so would prevent the customer from using the consumable again. To ensure, that offline usage information is regularly sent to blockchain network 100, each instrument 140 may require a new registration transaction, not only for the first time that a consumable is registered to a new instrument 140, but also for subsequent uses on the same instrument 140. For example, a number of uses may be encoded into the use code, described elsewhere herein, and software 142 on instrument 140 may use a counter to count down the encoded number of uses until depletion, and require a deregistration and/or new registration transaction whenever the number of uses is depleted.

In an embodiment, with each use of the consumable in step 340, an amount of kitcoins associated with the consumable code and representing the number of uses may be deducted in the transaction added to blockchain 120. Once all of the kitcoins, associated with a consumable code, have been depleted (i.e., the associated kitcoin amount is zero), any attempted transactions using that consumable code may be inferred to be improper. For example, such an attempted transaction may imply that the customer or some other party has refilled an empty reagent container or kit. However, it should be noted that, in some instances, a manufacturer may allow customers to refill certain consumables. In these instances, uses may continue to be recorded on blockchain 120, or may not be recorded on blockchain 120. In the former case, customers may be permitted to refill and use the refilled consumables, but may be required to expend kitcoins for each use.

In general, patient information should never be included in any of the machine-readable codes described herein. More generally, patient information should never be sent to blockchain network 100. This maintains patient privacy and ensures that the disclosed embodiments pose no threat to the security of patient information.

Advantageously, the use of blockchain 120 enables the manufacturer and customer to manage their inventory of consumables. While non-blockchain technology can perform a similar function, blockchain 120, by design, provides an extremely high level of security, traceability, and anti-fraud protection. For example, since blockchain 120 cannot be feasibly altered, there is no database of records that can be corrupted, tampered with, or otherwise altered. All transactions will be indelibly and indefinitely recorded on blockchain 120, providing a wealth of data for future analysis, data mining, and/or the like. However, it should be understood that other technology that provides an immutable ledger may be used instead of blockchain 120, such as a directed acyclic graph (e.g., Tangle™, in which kitcoins are analogous to the cryptocurrency IOTA).

As an example, as a reagent kit progresses from the manufacturer (e.g., Leica Biosystems™) to the customer and to depletion by the customer, every action along the way (e.g., the full history of the reagent kit) may be broadcast to blockchain network 100, and verified on blockchain 120. The fact that every transaction, including the usage of particular consumables, is recorded in blockchain 120 allows a manufacturer to prevent unauthorized refills and/or other uses of their consumables, track the amount and locations of orders and inventory, and/or the like. Blockchain 120 can also track the location of each use. Because usage is tracked, software 142 on instruments 140 can prevent a customer from using a consumable beyond its pre-allocated number of uses. Specifically, an instrument 140 may be configured (e.g., via software 142) to only perform a test using a reagent kit if all information from blockchain 120 is correct (e.g., the reagent kit is not registered to a different customer and/or instrument, the reagent kit has remaining tests, for example, as evidenced by a positive kitcoin amount associated with the reagent kit or in the customer's electronic wallet, the reagent kit is not expired, the reagent kit is not recalled, etc.).

Blockchain 120 also allows a customer to track orders and inventory of consumables, order new consumables when inventory is low, and/or the like. For example, the customer's system can automatically trigger a new order whenever the number of uses (e.g., kitcoins) remaining for a particular consumable is low (e.g., the associated amount of kitcoins fall below a predetermined threshold representing a certain number of uses) or depleted (e.g., the associated amount of kitcoins reaches zero).

2.2. Air Gap for Offline Instruments

Figure 4:
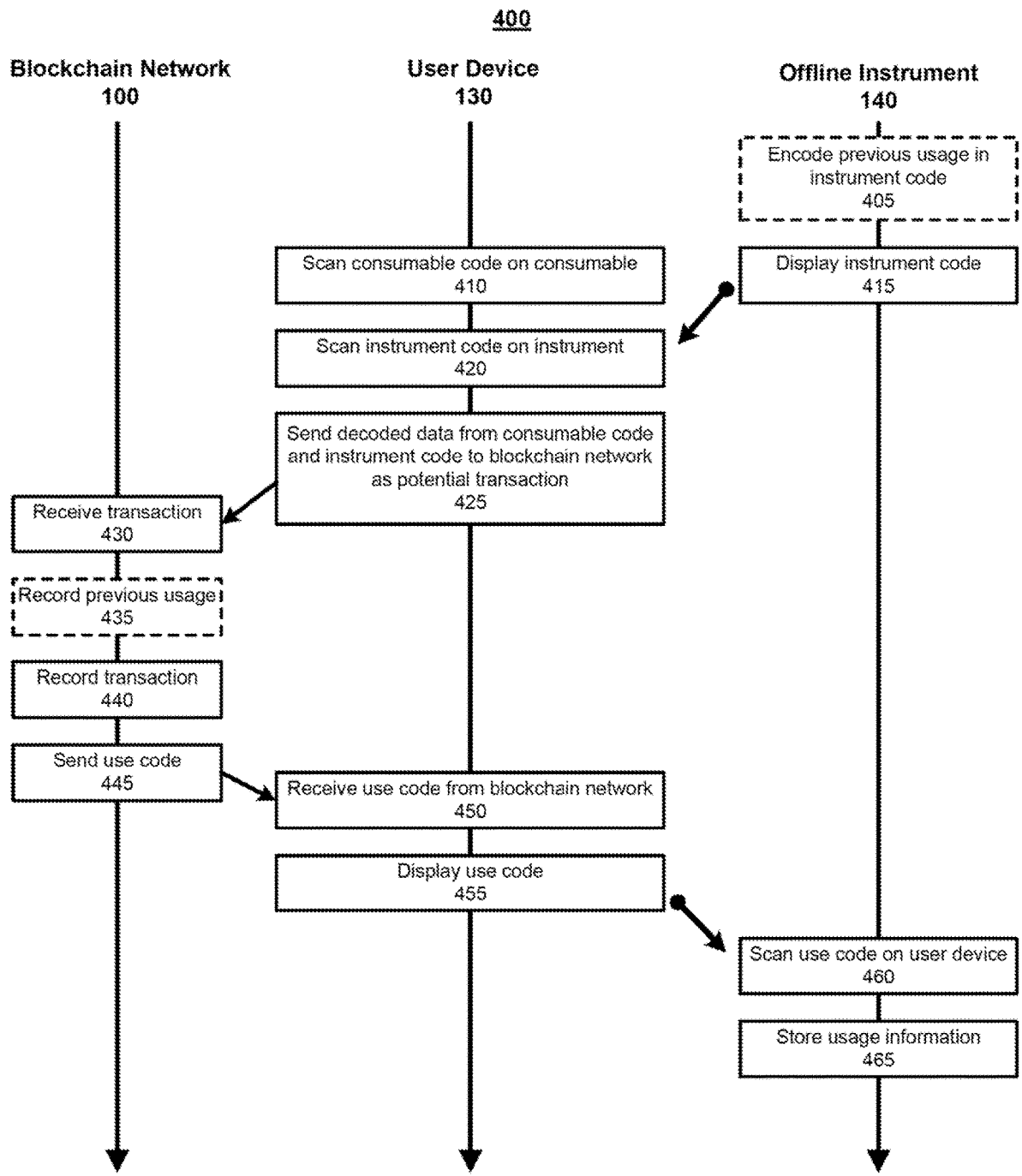
FIG. 4 is a timing diagram that illustrates a process for consumables tracking on offline instruments, according to an embodiment.

FIG. 4 is a timing diagram that illustrates a process 400 for consumables tracking on offline instruments, according to an embodiment. Specifically, process 400 may represent a portion of step 340 in process 300. While process 400 is illustrated with a certain arrangement and ordering of steps, process 400 may be implemented with fewer, more, or different steps and a different arrangement and/or ordering of steps. It should be understood that one or more processors of user device 130 may perform steps 410, 420, 425, 450, and 455 (e.g., via execution of client application 132), one or more processors of instrument 140 may perform steps 405, 415, 460, and 465 (e.g., via execution of software 142), and one or more processors at one or more nodes (e.g., systems 110) may perform steps 430, 435, 440, and 445.

In process 400, it is assumed that instrument 140 is offline (i.e., cannot communicate with blockchain network 100 or only has an intermittent connection to blockchain network 100), while user device 130 is online (i.e., can communicate with blockchain network 100). For example, instrument 140 may be a non-networked device, while user device 130 may be a smartphone or tablet with a wireless network connection (e.g., cellular or Wi-Fi™ connection), a personal computer (PC) with a wired or wireless network connection, a terminal with barcode readers (e.g., laser scanning wand) for tracking samples through a workflow (e.g., within an existing infrastructure of the Cerebro™ Sample Tracking System provided by Leica Biosystems™), or the like.

In step 410, user device 130 is utilized to scan the consumable code on the consumable to be used. For instance, if user device 130 comprises a camera, the user may use the camera of user device 130 to capture an image of a machine-readable code (e.g., barcode) on a reagent kit carrier. In an embodiment, client application 132 on user device 130 may control the camera to capture the image of the machine-readable code. Client application 132 may then decode the machine-readable code in the image using well-known techniques for identifying and decoding machine-readable codes in images. Alternatively, if user device 130 comprises a barcode reader (e.g., laser scanner), client application 132 or the user may control the barcode reader to scan the machine-readable code and decode the data in the machine-readable code. In an alternative embodiment in which the consumable code is human-readable (e.g., a numeric or alphanumeric character string), the consumable code could be input directly into client application 132 by the user (e.g., via one or more inputs in a graphical user interface).

In step 415, instrument 140 displays an instrument code. For example, instrument 140 may comprise a display screen, and one or more processors of instrument 140 may control the display screen to display a machine-readable code (e.g., barcode, QR code, etc.). Alternatively, the instrument code may be provided on a label that is affixed or otherwise associated with instrument 140 or printed directly on a housing of instrument 140. In either case, the instrument code may encode information that identifies the instrument (e.g., a unique numeric or alphanumeric identifier).

The instrument code may also encode additional information. For example, in an embodiment in which the instrument code is displayed on a display screen of instrument 140, instrument 140 may encode previous usage information into the instrument code in step 405. Specifically, as instrument 140 utilizes a consumable, usage information for that consumable (e.g., the number of tests, doses, or other runs) may be stored in a memory of instrument 140. Subsequently, when instrument 140 is requested to display the instrument code (e.g., in response to a user operation at instrument 140), instrument 140 may generate a new instrument code that encodes the instrument identifier as well as any new usage information (e.g., all usage information since the last time the instrument code was used). Notably, to protect patient privacy, the usage information and instrument code should not comprise any patient information.

In step 420, user device 130 is used to scan the instrument code for instrument 140. For instance, if user device 130 comprises a camera, the user may use the camera of user device 130 to capture an image of a machine-readable code (e.g., barcode) on the display screen of instrument 140, affixed to or printed on instrument 140, or otherwise associated with instrument 140. In an embodiment, client application 132 on user device 130 may control the camera to capture the image of the machine-readable code. Client application 132 may then decode the machine-readable code in the image using well-known techniques for identifying and decoding machine-readable codes in images. Alternatively, if user device 130 comprises a barcode reader (e.g., laser scanner), client application 132 or the user may control the barcode reader to scan the machine-readable code and decode the data in the machine-readable code. In an alternative embodiment in which the instrument code is human-readable, the instrument code could be input directly into client application 132 by the user (e.g., via one or more inputs in a graphical user interface).

In step 425, user device 130 sends the decoded data from the consumable code and the decoded data from the instrument code to blockchain network 100 as a potential transaction that registers the consumable, identified by the consumable code scanned in step 410, to instrument 140, identified in the instrument code. In step 430, blockchain network 100 (e.g., one or more systems 110 as nodes in blockchain network 100) receives the potential transaction.

In an embodiment, before being added to blockchain 120, a potential transaction must be validated. This validation may ensure that the consumable code and/or instrument code are valid. For example, the node (e.g., system 110) of blockchain 100 that processes the transaction may verify that the consumable code was issued or approved by the manufacturer of the consumable, for example, by checking blockchain 120 for a transaction representing the creation of the consumable by a particular party representing the manufacturer (e.g., an origination or shipping transaction comprising the manufacturer's identifier and the consumable code). In addition, the node may verify that there are uses remaining for the consumable (e.g., by checking that there are sufficient kitcoins associated with the consumable code or the customer). In step 440, if the transaction has been validated, the transaction is incorporated into blockchain 120, registering the use of the consumable, identified by the consumable code, to instrument 140, identified in the instrument code. If the transaction is not validated (e.g., due to an invalid consumable code, no remaining uses or kitcoins associated with the consumable code or customer, etc.), the transaction is not incorporated into blockchain 120.

In step 435, if the decoded data from the instrument code contained prior usage information, the prior use(s) represented by the prior usage information may be added as one or more transactions to blockchain 120. As discussed elsewhere herein, these transaction may deduct an amount of kitcoin associated with the consumable code identified in the prior usage information or the customer's electronic wallet, in accordance with how much of the corresponding consumable(s) was used, as specified in the prior usage information.

In step 445, blockchain network 100 sends a use code to user device 130. Blockchain network 100 (e.g., one or more systems 110 as nodes in blockchain network 100) may generate the use code based on the transaction recorded in step 440. The use code may be generated based on the consumable code, the instrument code, and/or any other information recorded in the transaction. If the transaction was not validated and recorded in step 440, blockchain network 100 either returns no use code or returns a use code that indicates that the transaction was not validated. In an embodiment, the use code may specify a number of uses that instrument 140 can consume before requiring another use code (e.g., obtained by another iteration of process 400 that, for example, deregisters and then re-registers the consumable code to instrument 140).

In step 450, user device 130 receives the use code from blockchain network 100. User device 130 may then encode the use code, and optionally additional information, into a machine-readable code (e.g., barcode, QR code, etc.), and display the machine-readable code on a display screen of user device 130 in step 455.

In step 460, instrument 140 scans the machine-readable code, which comprises the encoded use code, displayed on the display screen of user device 130. In an embodiment in which instrument 140 comprises a camera, software 142 on instrument 140 may control a camera to capture an image of the machine-readable code on the display screen of user device 130. Software 142 may then decode the machine-readable code in the image using well-known techniques for identifying and decoding machine-readable codes in images. Alternatively, if instrument 140 comprises a barcode reader (e.g., laser scanner), software 142 or the user may control the barcode reader to scan the machine-readable code and decode the data in the machine-readable code. In an alternative embodiment in which the use code is human-readable, the use code could be input directly into instrument 140 by the user (e.g., via one or more inputs in a graphical user interface).

In either case, instrument 140 may validate the use code. In an embodiment, the use code is encrypted and decrypted using a private key system (e.g., Pretty Good Privacy (PGP), Signal Protocol, etc.). For example, software 142 on instrument 140 may decrypt the use code using a private key (e.g., stored in a memory of or accessible to instrument 140). Software 142 may then check the consistency of the decrypted data, including, without limitation, a lot number, date of manufacture, date of use code generation, laboratory-allocated serial number of the instrument 140 being used, laboratory-allocated identification number of the user device 130 being used, and/or the like. Alternatively or additionally, in a non-technical implementation, the details of the consumable (e.g., reagent) may be published in the logs generated by the laboratory in which the consumable is being used. Most laboratories are held to stringent quality standards, and are required to document each step. In this case, any discrepancy in the machine-generated logs that is subsequently modified by hand may be used as the basis to raise a red flag for auditors.

If instrument 140 validates the use code, instrument 140 permits usage of the consumable associated with the consumable code, scanned in step 410. Since instrument 140 is offline, it cannot broadcast usage transactions (e.g., deducting kitcoins associated with the consumable or customer) to blockchain network 100 in real time. Thus, as the consumable is used, instrument 140 may instead store usage information about the consumable in step 465. This usage information may comprise the consumable code or other identifier associated with the consumable in association with the number of uses. This usage information may then be incorporated into a subsequent instrument code (e.g., in step 405) to be incorporated as one or more transactions into blockchain 120 at a future time. Thus, even though instrument 140 is offline, the usage of consumables in instrument 140 can still be managed by blockchain 120.

It should be understood that offline instrument 140 cannot use a consumable without a use code. Similarly, if instrument 140 cannot validate the use code or the use code indicates that the transaction was not validated and recorded in step 440, instrument 140 cannot use the consumable. In other words, instrument 140 cannot use a consumable without a valid use code that permits use of the consumable. This prevents instrument 140 from using improper (e.g., recalled, refilled, counterfeit, etc.) consumables.

In an embodiment, the use code may encode restrictions on usage of the particular consumable, scanned in step 410. For instance, in the event of a recall of a particular reagent for use in a particular test, the use code may specify that the particular reagent cannot be used in the particular test. Thus, software 142 in instruments 140 may decode the recall information from the use code and responsively prohibit the performance of the particular test using the particular reagent, while still allowing other tests to be performed using the particular reagent. In the event of a complete recall for the particular reagent, software 142 in instruments 140 may prevent any use of the reagent. Alternatively or additionally, software 142 may responsively notify the user of instrument 140 (e.g., on a display screen of instrument 140) about the recall. For instance, software 142 may pause an entire workflow until the recall notice is acknowledged (e.g., by a user confirming that he or she has read and understands the recall notice via one or more inputs in a graphical user interface displayed on the display screen of instrument 140).

In essence a particular consumable (e.g., reagent or reagent kit) or set of consumables (e.g., lot, type, etc.) can be remotely disabled, either completely or selectively. Specifically, a disabling transaction can be added to blockchain 120, such that no instrument 140 can utilize the consumable(s) that are the subject of the transaction. For instance, in the case of an offline instrument 140, no new registration transactions will be validated and recorded in step 440, and either no use code will be provided in steps 445-455, or the use code provided to instrument 140 in step 460 may comprise a restriction indicating that the consumable cannot be used. In the former case, a notification may be displayed on the display screen of user device 130 (e.g., within a graphical user interface of client application 132), instead of the use code. In the latter case, a notification may be displayed on the display screen of instrument 140. In both cases, the notification may notify the user that the consumable should be discarded, returned to the manufacturer, retained but not used, or the like.

Notably, while process 400 could be performed for online instruments 140, it would not typically be necessary for online instruments. In an embodiment, instruments 140 could comprise the same software 142, regardless of whether they are online or offline. In the event that software 142 detects that instrument 140 is offline (e.g., based on a user-specified setting, based on a system flag, by unsuccessfully attempting to ping a known uniform resource locator (URL), etc.), instrument 140 may perform the offline processing illustrated in process 400. However, in the event that software 142 detects that instrument 140 is online, instrument 140 may perform online processing. In the online processing, instrument 140 may directly scan and decode the consumable code from the consumable, send the decoded data to blockchain network 100, along with its instrument identifier and/or additional information, and receive the use code from blockchain network 100, without requiring a user device 130 to fill the air gap. In addition, in the online processing, instrument 140 could send usage information to blockchain network 100 (i.e., to be recorded as transactions in blockchain 120) in real time or near real time, as the consumable is used.

In an embodiment, a consumable may be deregistered from an instrument 140 using a similar process as process 400. For example, as the consumable is unloaded from instrument 140, instrument 140 may encode any previous usage information recorded in step 465 into an instrument code in step 405, and display the instrument code in step 415. The user may utilize user device 160 to scan the consumable code in step 410, scan the instrument code in step 420, and send the decoded data from the consumable and instrument codes to blockchain network 120. This information may then be used by blockchain network 120 to record a transaction that deregisters the consumable from the particular instrument 140, such that the consumable may be registered to a different instrument 140 or the same instrument 140 in the future.

2.3. Consumable-Specific Information

In an embodiment, additional information may be associated with consumable codes over time. Naturally, the machine-readable codes applied to consumables (e.g., reagent containers, reagent kits, etc.) cannot incorporate new information without being reprinted and reapplied to the consumables. However, additional information may be associated with the consumable codes, encoded into the machine-readable codes, such that the additional information can be retrieved based on the machine-readable code. In this manner, the information associated with a machine-readable code applied to a consumable may expand or otherwise change over time without having to change and reapply the machine-readable code to the consumable.

This additional information may include, without limitation, each location at which the machine-readable code was scanned, the temperature at one or more locations, and/or the like. The additional information may be added to blockchain 120 in a transaction (e.g., in addition to or within a transaction representing a scan, such as a waypoint scan during shipping).

As an example of how this information may used, reagent kits are generally rated for a certain temperature range, and should not be stored outside of that temperature range beyond a certain time period (e.g., three days). However, to save costs, manufacturers may ship the reagent kits without refrigeration. When a shipment of a reagent kit arrives at a customer, the additional information may be derived from the transactions in blockchain 120 that are associated with that reagent kit's consumable code. This information, which may comprise location, time, and temperature for a plurality of waypoints, may then be used to determine whether or not the reagent kit was stored outside of the rated temperature range for longer than a specified time period. If so, the customer may be notified to discard the reagent kit or shorten its expiration date to account for deterioration caused by this deficiency during shipping.

2.4. Kitcoins

In an embodiment, kitcoins may exist independently from consumables. For example, a particular consumable may be treated as an electronic "wallet," with the unique consumable code acting as the address of the electronic wallet. Initially, a consumable may be given to a customer for free, but without any kitcoins in its electronic wallet. The customer can then purchase kitcoins (e.g., by broadcasting a transaction that transfers kitcoins to the electronic wallet representing the consumable), representing uses (e.g., runs), in order to use the consumable. Such an implementation reduces inventory costs, since the value of the consumable may be nominal, whereas the kitcoins generate profit. In addition, buffer stocks of consumables can be stored at customers' facilities or local distribution points, without concerns about inventory or scrap costs.

2.5. Loyalty Program

In an embodiment, customers who provide nodes (i.e., system 110) within blockchain network 100 may be rewarded with kitcoins in exchange for their computing power. For example, kitcoins may be mined by customers similarly to how Bitcoins are mined. In exchange for generating a valid block of transactions to be added to blockchain 120, the customer may be rewarded with a certain amount of kitcoins. While kitcoin mining is not limited to customers, it should be understood that third parties, who do not utilize the consumables that are the subject of blockchain 120, may not assign any intrinsic value to kitcoins (but could earn value by trading in kitcoins).

In an embodiment, customers may be rewarded with kitcoins for other activities. Such activities may include attending tradeshows, purchasing products from the manufacturer (e.g., Leica Biosystems™), bookings for preventative maintenance, properly servicing their instruments 140, and/or the like.

Regardless of how a customer earns kitcoins, the customer may use those kitcoins in order to utilize consumables. For example, the customer may expend a certain amount of kitcoins for each use of a consumable (e.g., each test or other run).

2.6. Analysis

The transactions, including uses of consumables, recorded in blockchain 120, can provide valuable insight into the consumables themselves. Thus, in an embodiment, the transactions may be analyzed (e.g., by a manufacturer), for example, for the purposes of customer relationship management.

For example, reagents are often rated for a minimum number of uses. If a customer complains that the minimum number of uses was not obtained from a reagent, the manufacturer can confirm or refute the customer's complaint based on usage transactions, recorded on blockchain 120, for the particular reagent. Specifically, the manufacturer may retrieve any usage transactions on blockchain that comprise the consumable code for the reagent, and count the number of actual uses. If the number of actual uses is less than the rated minimum number of uses, the manufacturer can confirm and redress the customer's complaint. Otherwise, if the number of actual uses is equal to or greater than the rated minimum number of uses, the manufacturer has hard evidence that the complaint is baseless.

In addition, the manufacturer could use this usage information over a plurality of consumables to reduce overfill. For instance, if the transactions on blockchain 120 indicate that a reagent is consistently providing an actual number of uses that far exceeds the rated minimum number of uses for that reagent, the manufacturer can appropriately reduce the volume of that reagent. This can save unnecessary costs associated with overfill.

2.7. Instrument History

In an embodiment, since all uses of consumables by a particular instrument 140 are recorded on blockchain 120, instruments 140 can also be tracked by blockchain 120. For example, the usage history of each instrument 140 can be inferred from the usage transactions associated with that instrument 140 (e.g., transactions comprising an identifier of the instrument 140). This usage history can be used to produce service and/or repair information (e.g., scheduling a service or repair). For example, assume that the manufacturer recommends that instruments 140 be serviced (e.g., routine checkup, replacement of a particular part, etc.) every one-thousand uses. A software service of the manufacturer and/or customer may continually check blockchain 120 and compute the amount of uses, recorded in transactions on blockchain 120, for each instrument 140. When the amount of uses for a particular instrument 140 reaches one thousand or is within a predetermined range of one thousand, the software service can notify a user of the manufacturer and/or customer, automatically schedule a service of instrument 140, prevent instrument 140 from using any more consumables until it has been serviced, and/or the like. In addition, any services of an instrument 140 can be recorded in blockchain 120 as a transaction (e.g., a service transaction identifying the instrument 140), so that there is a service record for each instrument 140 within blockchain 120.

The above description of the disclosed embodiments is provided to enable any person skilled in the art to make or use the invention. Various modifications to these embodiments will be readily apparent to those skilled in the art, and the general principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

Combinations, described herein, such as "at least one of A, B, or C," "one or more of A, B, or C," "at least one of A, B, and C," "one or more of A, B, and C," and "A, B, C, or any combination thereof" include any combination of A, B, and/or C, and may include multiples of A, multiples of B, or multiples of C. Specifically, combinations such as "at least one of A, B, or C," "one or more of A, B, or C," "at least one of A, B, and C," "one or more of A, B, and C," and "A, B, C, or any combination thereof" may be A only, B only, C only, A and B, A and C, B and C, or A and B and C, and any such combination may contain one or more members of its constituents A, B, and/or C. For example, a combination of A and B may comprise one A and multiple B's, multiple A's and one B, or multiple A's and multiple B's.

What is claimed is:

1. An apparatus comprising:
a processing system for processing a tissue or staining the tissue; and
at least one hardware processor configured to:
obtain a use code from a blockchain network, the use code generated based on a consumable code associated with a consumable and an instrument code that identifies the processing system;

wherein the use code indicates one or more restrictions;
send usage information to the blockchain network, the usage information indicating usage of the consumable with the processing system;
control the processing system to, based on the one or more restrictions, prevent or limit the usage of the consumable in processing the tissue or staining the tissue in the processing system.

2. The apparatus of claim 1, wherein the consumable code uniquely identifies the consumable and corresponds to a number of runs, tests, or uses of the consumable.

3. The apparatus of claim 1, wherein the use code indicates a number of runs, and wherein the at least one hardware processor is configured to limit the usage of the consumable so as not to exceed the number of runs.

4. The apparatus of claim 1, wherein the use code indicates a recall for one or more types of runs, and wherein the at least one hardware processor is configured to prohibit the one or more types of runs during the usage of the consumable.

5. The apparatus of claim 1, wherein the processing system comprises a communication interface communicatively connected to the at least one hardware processor to obtain the use code from and send usage information to at least one node of the blockchain network using wired and/or wireless communication.

6. The apparatus of claim 1, wherein obtaining the use code from the blockchain network comprises:
scanning a machine-readable code displayed by a user device that is configured to receive the use code from the blockchain network, wherein the machine-readable code is based on the use code, and
decoding the use code from the machine-readable code.

7. The apparatus of claim 1, wherein sending usage information to the blockchain network comprises:
storing usage information during usage of the consumable,
generating a machine-readable code based on the usage information, and displaying the machine-readable code on a display for communication of the usage information to the blockchain network via a user device.

8. The apparatus of claim 1, wherein the at least one hardware processor is further configured to validate the use code, prior to the usage of the consumable, by:
decrypting data from the use code using a private key, and
checking a consistency in the decrypted data.

9. The apparatus of claim 1, wherein the consumable comprises a reagent.

10. A method comprising:
obtaining a use code from a blockchain network, the use code generated based on a consumable code associated with a consumable and an instrument code that identifies a processing system that is configured to process a tissue or stain the tissue;
wherein the use code indicates one or more restrictions;
sending usage information to the blockchain network, the usage information indicating usage of the consumable with the processing system; and
control the processing system to, based on the one or more restriction, prevent or limit the usage of the consumable in processing the tissue or staining the tissue in the processing system.

11. The method of claim 10, wherein obtaining the use code from the blockchain network comprises:
scanning a machine-readable code displayed by a user device that is configured to receive the use code from the blockchain network, wherein the machine-readable code is based on the use code, and
decoding the use code from the machine-readable code.

12. The method of claim 10, wherein sending usage information to the blockchain network comprises:
storing usage information during usage of the consumable,
generating a machine-readable code based on the usage information, and displaying the machine-readable code on a display for communication of the usage information to the blockchain network via a user device.

13. The method of claim 10, further comprising:
decrypting data from the use code using a private key;
checking a consistency in the decrypted data; and
validating the use code based on the consistency in the decrypted data.

14. The method of claim 10, further comprising limiting the usage of the consumable according to a number of runs indicated by the use code, wherein the consumable code is associated with a number of runs for which the consumable is rated.

15. A non-transitory computer-readable medium having instructions stored therein, wherein the instructions, when executed by at least one hardware processor, cause the at least one hardware processor to perform a method comprising:
obtaining a use code from a blockchain network, the use code generated based on a consumable code associated with a consumable and an instrument code that identifies a processing system that is configured to process a tissue or stain the tissue;
wherein the use code indicates one or more restrictions;
sending usage information to the blockchain network, the usage information indicating usage of the consumable with the processing system; and
controlling the processing system to, based on the one or more restrictions, prevent or limit the usage of the consumable in processing the tissue or staining the tissue in the processing system.

16. The non-transitory computer-readable medium of claim 15, wherein obtaining the use code from the blockchain network comprises:
scanning a machine-readable code displayed by a user device that is configured to receive the use code from the blockchain network, wherein the machine-readable code is based on the use code, and
decoding the use code from the machine-readable code.

17. The non-transitory computer-readable medium of claim 15, wherein sending usage information to the blockchain network comprises:
storing usage information during usage of the consumable,
generating a machine-readable code based on the usage information, and
displaying the machine-readable code on a display for communication of the usage information to the blockchain network via a user device.

18. The non-transitory computer-readable medium of claim 15, wherein the method further comprises:
decrypting data from the use code using a private key;
checking a consistency in the decrypted data; and
validating the use code based on the consistency in the decrypted data.

19. The non-transitory computer-readable medium of claim 15, wherein the method further comprises limiting the usage of the consumable according to a number of runs indicated by the use code, wherein the consumable code is associated with a number of runs for which the consumable is rated.

\* \* \* \* \*